(12) United States Patent
Crawford

(10) Patent No.: US 7,972,309 B2
(45) Date of Patent: Jul. 5, 2011

(54) NEEDLE ASSEMBLY

(75) Inventor: Jaimeson William Maclean Crawford, Demarest, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/694,568

(22) Filed: Jan. 27, 2010

(65) Prior Publication Data

US 2010/0168614 A1 Jul. 1, 2010

Related U.S. Application Data

(60) Continuation of application No. 11/170,130, filed on Jun. 29, 2005, now Pat. No. 7,678,076, which is a division of application No. 10/173,928, filed on Jun. 17, 2002, now abandoned.

(60) Provisional application No. 60/377,399, filed on May 2, 2002.

(51) Int. Cl.
*A61M 5/178* (2006.01)
(52) U.S. Cl. ............... 604/164.01; 604/170.01; 600/576
(58) Field of Classification Search .................. 604/110, 604/164.01, 263, 161, 164.08, 170.01, 170.02, 604/171, 177; 600/576
See application file for complete search history.

(56) References Cited

U.S. PATENT DOCUMENTS

| | | | |
|---|---|---|---|
| 4,828,547 A | 5/1989 | Sahi et al. |
| 4,887,998 A | 12/1989 | Martin et al. |
| 5,009,642 A | 4/1991 | Sahi |
| 5,120,320 A | 6/1992 | Fayngold |
| 5,192,275 A | 3/1993 | Burns |
| 5,356,392 A | 10/1994 | Firth et al. |
| 5,472,430 A | 12/1995 | Vaillancourt et al. |
| 5,476,106 A | 12/1995 | Gartz |
| 5,605,544 A | 2/1997 | Tsao |
| 5,718,239 A | 2/1998 | Newby et al. |
| 5,755,673 A | 5/1998 | Kinsey |
| 5,810,775 A | 9/1998 | Shaw |
| 5,893,845 A | 4/1999 | Newby et al. |
| 5,951,520 A | 9/1999 | Burzynski et al. |
| 6,077,244 A | 6/2000 | Botich et al. |
| 6,077,253 A | 6/2000 | Cosme |
| 6,146,337 A | 11/2000 | Polidoro et al. |
| 6,224,576 B1 | 5/2001 | Thorne et al. |
| 6,254,574 B1 | 7/2001 | Burzynski et al. |
| 6,264,619 B1 | 7/2001 | Ferguson |
| 6,436,070 B1 | 8/2002 | Botich et al. |
| 6,475,189 B1 | 11/2002 | Lilley, Jr. |
| 6,544,239 B2 | 4/2003 | Kinsey et al. |
| 6,616,637 B2 | 9/2003 | Alexander et al. |
| 6,629,956 B1 | 10/2003 | Polidoro et al. |
| 6,761,704 B2 | 7/2004 | Crawford |
| 2002/0147428 A1 | 10/2002 | Chang et al. |
| 2003/0055381 A1 | 3/2003 | Wilkinson |

(Continued)

FOREIGN PATENT DOCUMENTS

DE 29620187 2/1997

(Continued)

*Primary Examiner* — Kevin C Sirmons
*Assistant Examiner* — Laura C Schell
(74) *Attorney, Agent, or Firm* — The Webb Law Firm

(57) ABSTRACT

A blood collection set including a non-patient needle assembly interconnected with an intravenous needle assembly through tubing is provided. The non-patient needle assembly includes a hub assembly adapted for mounting with a blood collection set, and an internal blunting member including a blunted tip. The non-patient needle assembly further includes an external cannula concentric with the internal blunting member and including a non-patient puncture tip adjacent the blunted tip. The external cannula is axially displaceable with respect to the hub assembly between a first retracted position in which the non-patient puncture tip extends beyond the blunted tip and a second activated position in which blunted tip extends beyond the non-patient puncture tip.

8 Claims, 5 Drawing Sheets

U.S. PATENT DOCUMENTS

| | | |
|---|---|---|
| 2003/0060772 A1 | 3/2003 | Swenson |
| 2003/0208139 A1 | 11/2003 | Crawford |
| 2003/0208160 A1 | 11/2003 | Crawford |
| 2003/0208161 A1 | 11/2003 | Crawford |
| 2003/0208162 A1 | 11/2003 | Crawford |
| 2004/0030291 A1 | 2/2004 | Holdaway et al. |

FOREIGN PATENT DOCUMENTS

| | | |
|---|---|---|
| EP | 1110576 | 12/2000 |
| FR | 2564726 | 11/1985 |
| WO | 9739786 | 10/1997 |
| WO | 9842393 | 10/1998 |
| WO | 0020058 | 4/2000 |
| WO | 0023130 | 4/2000 |

NEEDLE ASSEMBLY

CROSS REFERENCE TO RELATED APPLICATIONS

This application is a continuation of U.S. patent application Ser. No. 11/170,130 filed Jun. 29, 2005, now U.S. Pat. No. 7,678,076, which is a divisional application of U.S. patent application Ser. No. 10/173,928 filed Jun. 17, 2002, (now abandoned), which claims priority to U.S. Provisional Patent Application No. 60/377,399 filed May 2, 2002, the entire disclosures of each of which are hereby incorporated by reference.

BACKGROUND OF THE INVENTION

1. Field of the Invention

The present invention relates to needle assemblies having a blunting element for safe and convenient handling. More particularly, the present invention relates to a non-patient needle assembly which includes a blunting element for the non-patient needle for use in connection with a blood collection set.

2. Description of Related Art

Disposable medical devices having piercing elements are typically used for administering a medication or withdrawing a fluid, such as blood collecting needles, fluid handling needles, and assemblies thereof. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after usage. Thus, these blood collection systems allow repeated use of the relatively expensive holder upon replacement of the relatively inexpensive needle and/or fluid collection tube. In addition to reducing the cost of collecting blood specimens, these blood collection systems also help minimize the production of hazardous medical waste.

Conventional intravenous tubing sets are commonly employed for use in connection with blood collection. A particularly useful intravenous tubing set for such application is the VACUTAINER® Brand Safety-Lok™ Blood Collection Set, available from Becton, Dickinson and Company of Franklin Lakes, N.J. Such a blood collection set includes an intravenous needle assembly attached to one end of a tube, with the other end of the tube connected to a blood collection needle assembly including a stopper puncture needle, or a "non-patient" puncture needle. In use, the intravenous needle assembly is inserted into the vein of a patient, and a tube holder is attached to the blood collection needle assembly. An evacuated tube is inserted into the tube holder, and the stopper puncture needle or non-patient puncture needle punctures the stopper of the tube, allowing blood to flow into the tube.

In order to reduce the risk of incurring an accidental needle-stick wound, protection of used needle tips becomes important. With concern about infection and transmission of diseases, methods and devices to enclose the used disposable needle have become very important and in great demand. Many arrangements have been designed for protecting used needle tips. For example, U.S. Pat. No. 5,120,320 to Fayngold and U.S. Pat. No. 5,192,275 to Burns disclose safety shields for use in connection with the intravenous needle assembly of such blood collection assemblies. The safety shield covers and protects the intravenous needle assembly after use. Also, PCT International Publication No. WO 98/42393 discloses a parenteral fluid transfer apparatus useful as a blood collection assembly, which includes an intravenous needle assembly having a rod or probe-like blunting member which is extendable beyond the tip of the intravenous needle tip to prevent accidental needle-stick wounds from occurring after use of the device. Such a device, however, does not provide protection for the second end of the needle at the non-patient end of the assembly.

Accordingly, a need exists for a blood collection set with a non-patient needle assembly which provides for safety blunting of the non-patient needle tip and which is simple to manufacture and easy to operate.

SUMMARY OF THE INVENTION

The present invention is directed to a non-patient safety needle assembly for mounting with a conventional intravenous blood collection set including a non-patient hub assembly having opposing first and second ends and a central opening extending through the hub assembly from the first end to the second end. The first end being adapted for mounting with a blood collection set. The needle assembly also includes an internal blunting member in fixed engagement with the non-patient hub assembly and extending through the central opening of the hub assembly, with the internal blunting member having a first end concentric with the non-patient hub assembly. The needle assembly also includes a second end of the blunting member having a blunted tip and an internal lumen extending through the internal blunting member from the first end of the blunting member to the blunted tip. The needle assembly further includes an external non-patient cannula concentric with the internal blunting member and axially displaceable within the non-patient hub assembly, with the external non-patient cannula including a non-patient puncture tip adjacent the blunted tip of the internal blunting member. The needle assembly further includes an external non-patient cannula adapted for axial displacement with respect to the non-patient hub assembly about the internal blunting member between a first retracted position in which the non-patient puncture tip extends beyond the blunted tip of the internal blunting member and a second activated position in which the blunted tip of the internal blunting member extends beyond the non-patient puncture tip of the external non-patient cannula. The needle assembly further includes a sleeve extending about the non-patient puncture tip, wherein the non-patient puncture tip can be inserted into and removed from a blood collection tube having a pierceable membrane while the external non-patient cannula is in the first retracted position.

The non-patient safety needle assembly may further include a carriage assembly integral with the external non-patient cannula and concentric with the internal blunting member, with the carriage assembly provided for slidable engagement with the non-patient hub assembly.

The non-patient safety needle assembly may further include a fitting for engagement with a blood collection set. The fitting may include a luer fitting.

The non-patient safety needle assembly may further include means for attaching the non-patient needle assembly to a holder capable of holding blood collection tubes. The attaching means may include threads extending circumferentially about the non-patient hub assembly.

The non-patient safety needle assembly may be configured such that the external non-patient cannula is axially displaceable between the first retracted position and the second activated position in a single axial direction. The non-patient safety needle assembly may further include a locking mechanism for preventing axial displacement of the external cannula from the second activated position to the first retracted position.

DETAILED DESCRIPTION

Figure 1:
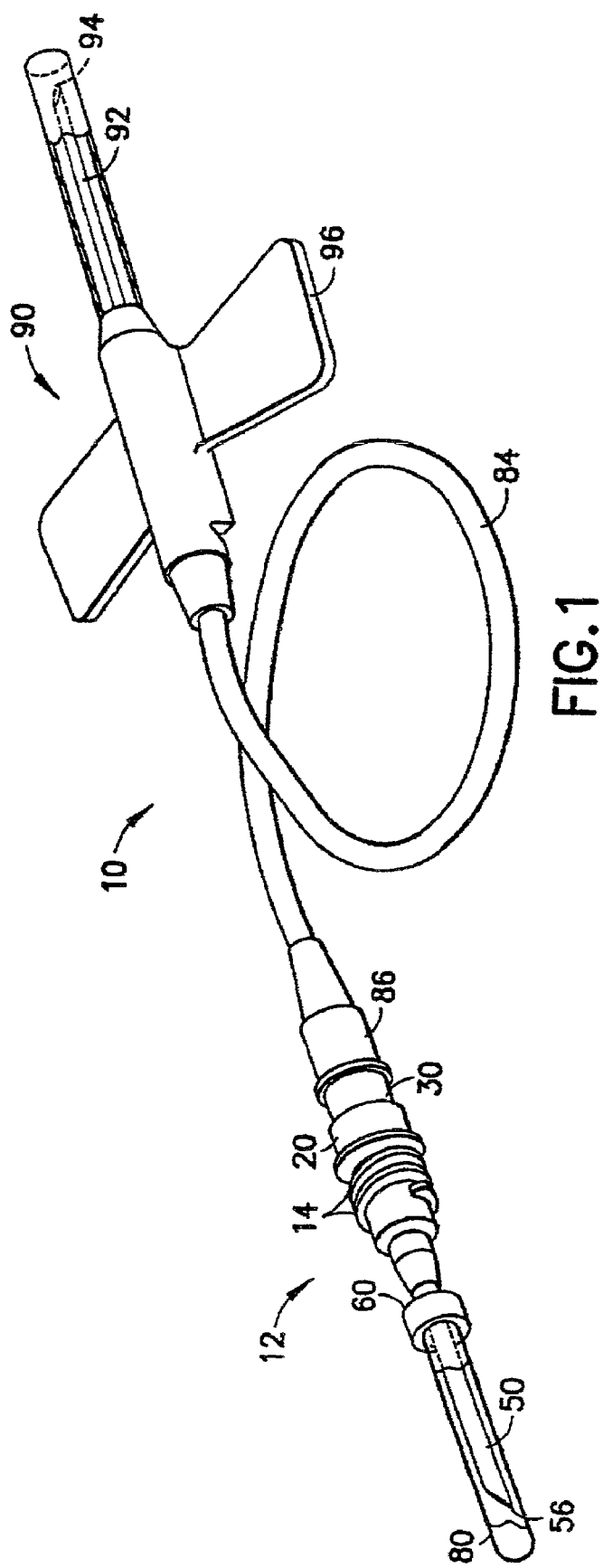
FIG. 1 is a perspective view of a blood collection set in accordance with the present invention, including a non-patient safety needle assembly attached to an intravenous needle assembly through tubing.

While the present invention is satisfied by embodiments in many different forms, there is shown in the drawings and will herein be described in detail, the preferred embodiments of the invention, with the understanding that the present disclosure is to be considered as examplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIG. 1 illustrates a blood collection set in accordance with the present invention and the related features. The present invention is generally described in terms of a blood collection set, and encompasses such a blood collection set as well as a non-patient safety needle assembly for use in such a blood collection set.

Blood collection set 10 is depicted generally including non-patient needle assembly 12 in engagement with a conventional intravenous blood collection assembly. Non-patient needle assembly 12 and the intravenous blood collection assembly include interrelating elements to provide for engagement therebetween. In particular, non-patient needle assembly 12 is interconnected with intravenous needle assembly 90 through tubing 84. Such interconnection may be provided through any method as is known in the art, such as through a luer fitting.

Intravenous needle assembly 90 includes an intravenous cannula 92 having an intravenous puncture tip 94, for insertion into the vein of a patient, for example, during a blood collection procedure. Intravenous needle assembly 90 further includes a butterfly-type wing assembly 96 for use in connection with positioning and placement of intravenous needle assembly 90 during a blood collection procedure, as is known in the art.

As noted, intravenous needle assembly 90 is interconnected through tubing 84 to non-patient needle assembly 12. In addition, non-patient needle assembly 12 may be provided with means for attachment to a separate holder (not shown) for use in connection with blood collection tubes, such as a snap fit attachment, or, more desirably, attachment threads 14 which engage a threaded section of the holder.

Non-patient needle assembly 12 of the present invention is shown more particularly at FIGS. 2-5. Non-patient needle assembly 12 includes hub assembly 20 having first end 22 and second end 24, with an internal opening 26 extending therethrough from first end 22 to second end 24. First end 22 of hub assembly 20 is adapted for mounting with tubing 84 of blood collection set 10. For example, hub assembly 20 may further include ferrule 30 extending from first end 22. Ferrule 30 may be integrally formed with hub assembly 20, or may be a separate member attached to hub assembly 20. Desirably, hub assembly 20 includes shoulder 34 at an internal opening within first end 22 for engagement with ferrule 30 such that ferrule 30 interfits within first end 22 and rests against shoulder 34 of hub assembly 20. Ferrule 30 includes an internal opening 36 extending therethrough, which is in fluid communication with internal opening 26 of hub assembly 20.

Non-patient needle assembly 12 further includes internal blunting member 40 in fixed engagement with hub assembly 20. Internal blunting member 40 is a generally tubular hollow structure which includes first end 42 and second end 44 with a central bore or internal lumen 48 extending through the length thereof. Internal lumen 48 allows fluid flow through needle assembly 12 during use. Second end 44 is blunted to form blunt tip 46 as an end portion, such that, under ordinary hand pressure, blunt tip 46 will not easily puncture human skin or other biological tissue.

Figure 3:
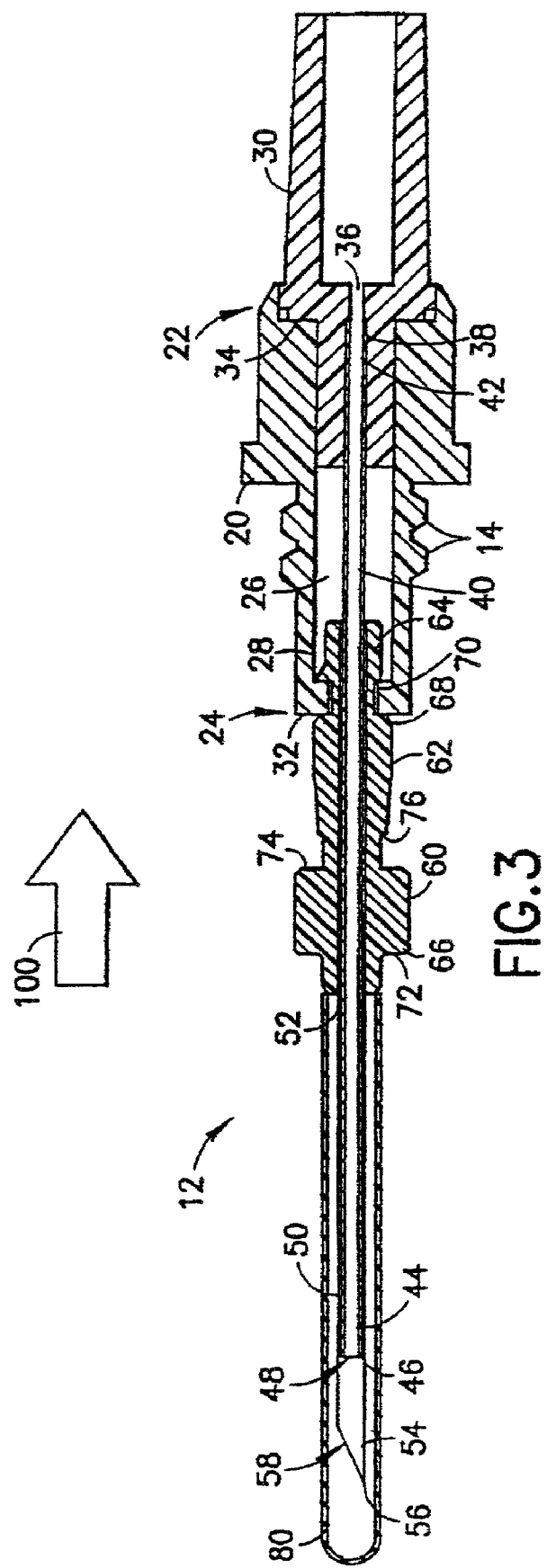
FIG. 3 is a side cross-sectional view of the non-patient safety needle assembly of FIG. 2 shown in a retracted position.

Internal blunting member 40 is provided in concentric relation with hub assembly 20. More particularly, first end 42 of internal blunting member 40 is positioned concentrically within internal opening 26 of hub assembly 20, while second end 44 of internal blunting member 40 extends axially from second end 22 of hub assembly 20. Internal lumen 48 is in fluid communication with internal opening 26 of hub assembly 20 and, in turn, internal opening 36 of ferrule 30. Internal blunting member 40 may be integrally formed with hub assembly 20, but is more desirably a separate member which is fixedly attached to hub assembly 20. In particular, as depicted in FIG. 3, first end 42 of internal blunting member 40 is provided within internal opening 26 of hub assembly 20 and abuts lip 38 of ferrule 30, which extends within first end 22 of hub assembly 20. In this manner, hub assembly 20, ferrule 30, and internal blunting member 40 form a single unitary structure.

Non-patient needle assembly 12 further includes external cannula 50 extending concentrically about internal blunting member 40. External cannula 50 is adapted for axial movement with respect to hub assembly 20, as will be described in more detail herein. External cannula 50 includes a first end 52 and a second end 54, with a central bore or internal lumen 58 extending through the length thereof. Second end 54 includes non-patient puncture tip 56, which is provided in the form of a needle tip for puncturing a stopper such as is used in an evacuated tube, for example, during a blood collection procedure. External cannula 50 is further provided with an elastomeric sleeve 80 extending about second end 44 and covering non-patient puncture tip 56, as is generally known in the art.

Figure 2:
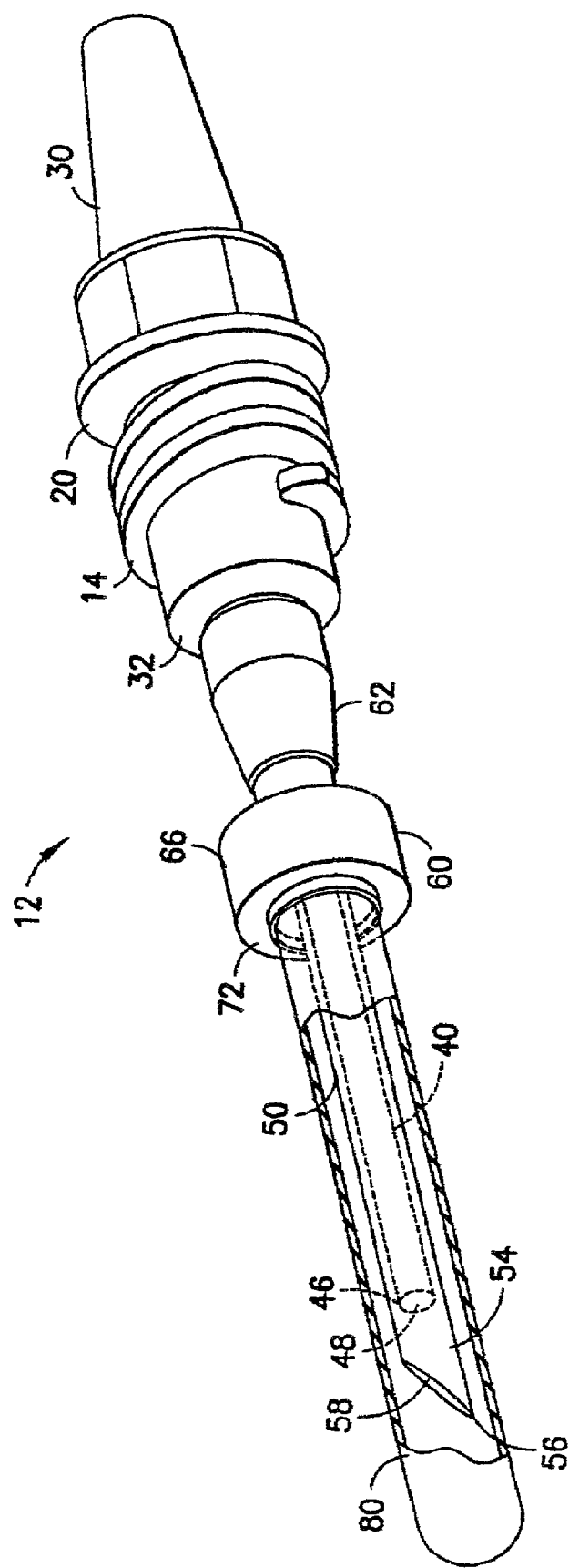
FIG. 2 is a perspective view of a non-patient safety needle assembly in accordance with the present invention shown in a retracted position.
Figure 4:
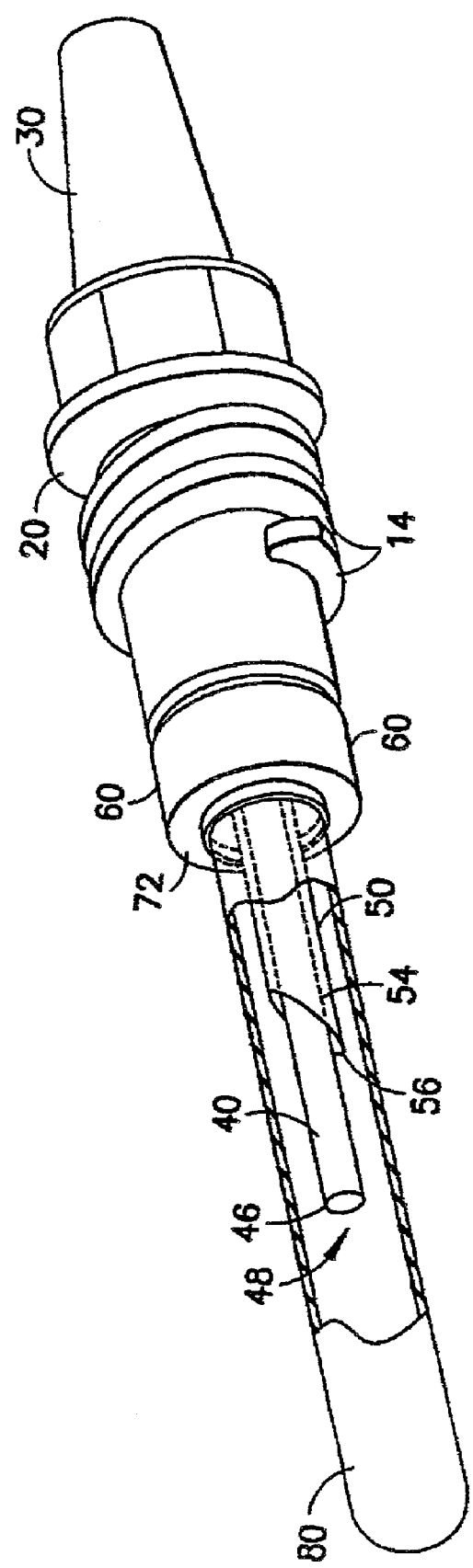
FIG. 4 is a perspective view of the non-patient safety needle assembly of FIG. 2 shown in an activated blunted position.
Figure 5:
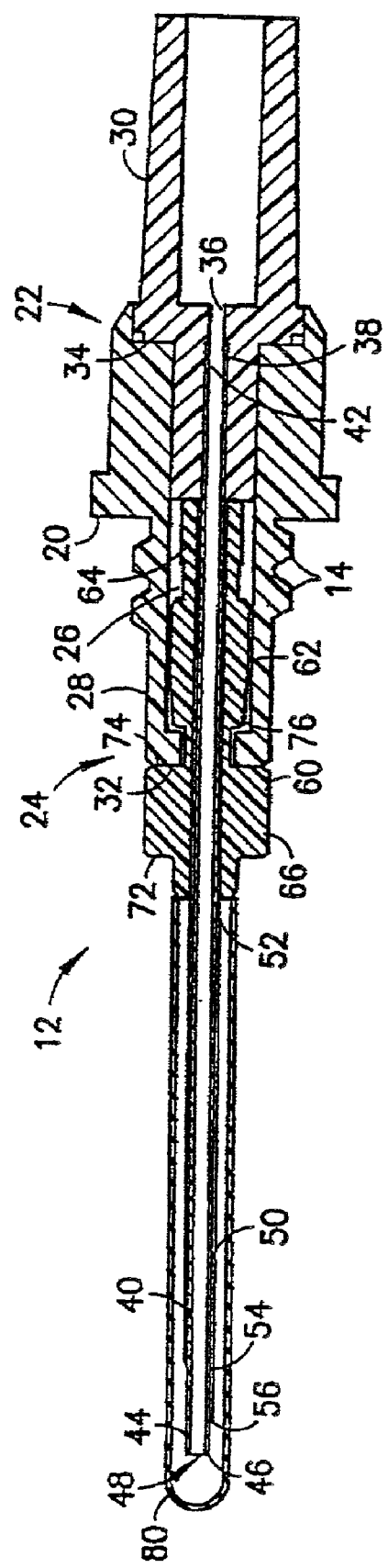
FIG. 5 is a side cross-sectional view of the non-patient safety needle assembly of FIG. 4 in an activated blunted position.

As best depicted in FIGS. 2 and 3, second end 54 of external cannula 50 is adjacent second end 44 of internal blunting member 40. External cannula 50 is axially slidable along second end 44 of internal blunting member 40 within the internal lumen 58 of external cannula 50. As such, external cannula 50 is axially displaceable with respect to hub assembly 20, since internal blunting member 40 is in fixed engagement with hub assembly 20. The inner diameter of external cannula 50 is substantially the same as the outer diameter of second end 44 of internal blunting member 40. As such, external cannula 50 and internal blunting member 40 are dimensioned and configured for a close fit so that blunt tip 46 of internal blunting member 40 lies flat against the internal surface of second end 54 of external cannula 50 within internal lumen 58 when non-patient needle assembly 12 is in a retracted position, as shown in FIGS. 2 and 3, and so that non-patient puncture tip 56 lies flat against the external surface of second end 44 of internal blunting member 40 when non-patient needle assembly 12 is in an activated position, as shown in FIGS. 4 and 5.

It may be desirable to lubricate the mating surfaces of external cannula 50 and internal blunting member 40, as well as to provide a seal between them to prevent the unwanted flow of air bubbles. Accordingly, a drop of viscous sealant-lubricant, such as petroleum jelly, may be provided about the mating surfaces thereof.

As noted, external cannula 50 is adapted for axial movement with respect to hub assembly 20. For example, external cannula 50 may be axially slidable within internal opening 26 of hub assembly 20 between a first retracted position in which non-patient puncture tip 56 extends beyond blunt tip 46, and a second activated position in which blunt tip 46 extends beyond non-patient puncture tip 56. More particularly, axial movement of external cannula 50 within internal opening 26 of hub assembly 20 in a direction of arrow 100 causes external cannula 50 to axially displace with respect to hub assembly 20. Since internal blunting member 40 is fixedly attached to hub assembly 20, such axial displacement causes external cannula 50 to axially slide along second end 44 of internal blunting member 40. Since second end 54 of external cannula 50 is adjacent second end 44 of internal blunting member 40 and non-patient puncture tip 56 extends beyond blunt tip 46, such axial movement causes second end 54 of external cannula 50 to axially displace with respect to second end 44 of internal blunting member 40, which causes non-patient puncture tip 56 to slide about internal blunting member 40 such that blunt tip 46 extends beyond non-patient puncture tip 56, as depicted in FIGS. 4 and 5. As such, non-patient puncture tip 56 is blunted.

Slidable engagement of external cannula 50 and hub assembly 20 may be effected through carriage assembly 60. Carriage assembly 60 is concentric with external cannula 50, and is provided for slidable engagement within internal opening 26 of hub assembly 20. Carriage assembly 60 may be integral with external cannula 50, or may be a separate member which is fixedly adhered to external cannula 50 such as through the use of an adhesive. Carriage assembly 60 is defined by a generally tubular body, although other shapes or configurations may be apparent to those skilled in the art.

Carriage assembly 60 includes a central nub portion 62, a forward portion 64 and a rear portion 66. As shown in FIGS. 2 and 3, forward portion 64 of carriage assembly 60 is positioned within internal opening 26 of hub assembly 20 when non-patient needle assembly 12 is assembled and in the retracted position. Forward portion 64 of carriage assembly 60 includes a surface 70 for interference engagement with shoulder 28 of hub assembly 20. Such interference engagement prevents carriage assembly 60, and therefore external cannula 50 which is attached thereto, from being easily removed or disassembled from hub assembly 20 after assembly thereof.

Central nub portion 62 includes a tapered surface 68 extending circumferentially thereabout. Tapered surface 68 provides an interference engagement with face 32 at second end 24 of hub assembly 20, preventing axial displacement of carriage assembly 60 with respect to hub assembly 20 without a force exerted thereon, as will be described in more detail herein.

Carriage assembly 60 further includes rear face 72 which is adapted for engagement with the top surface of a blood collection tube during use. As will be discussed with respect to the use and operation of non-patient needle assembly 12, rear face 72 provides a mechanism for activating non-patient needle assembly 12, thereby axially displacing external cannula 50 with respect to hub assembly 20 between a first retracted position and a second activated position.

External cannula 50 and hub assembly 20 may be reversibly axially displaceable with respect to each other, such that external cannula 50 may displace with respect to hub assembly 20 from either the first retracted position to the second activated position or from the second activated position to the first retracted position. In preferred embodiments, external cannula 50 is axially displaceable with respect to hub assembly 20 in only a single direction from the first retracted position to the second activated position. As such, non-patient needle assembly 12 may be provided with means for preventing axial displacement of external cannula 50 from the second activated position to the first retracted position once it has been activated, such as a locking mechanism. For example, central nub portion 62 may further include a surface 76 which extends circumferentially about central nub portion 62 for interference engagement with shoulder 28 of hub assembly 20 after activation of non-patient needle assembly 12 from the first retracted position to the second activated position. Such interference engagement prevents axial movement of carriage assembly 60 with respect to hub assembly 20 in a direction opposite arrow 100 after movement from the first retracted position to the second activated position.

Non-patient needle assembly 12 may be provided with means for indicating movement of external cannula 50 with respect to hub assembly 20 between the first retracted position and the second activated position. Such means may be a visible, audible, and/or tactile indicator identifying movement between the first retracted position and the second extended position. For example, in one particular embodiment, a tactile indication is accomplished through the interference engagement of tapered surface 68 with face 32 of hub assembly 20, as well as the interference engagement of front face 74 of carriage assembly 60 with face 32 of hub assembly 20. For example, when carriage assembly 60 is axially displaced in a direction of arrow 100, the user will detect an audible and/or tactile detection through the forcing of tapered surface 68 of carriage assembly 60 past face 32 of hub assembly 20. When carriage assembly 60 is completely displaced to the second activated position, a further audible and/or tactile detection will be detected by front face 74 of carriage assembly 60 abutting with face 32 of hub assembly 20.

Non-patient needle assembly 12 may be provided with a needle cover (not shown) for covering non-patient puncture tip 56 of external cannula 50 prior to assembling of non-patient needle assembly 12 with a needle holder. Such a needle cover may be constructed of rigid polymeric material. This needle cover may be attached to non-patient needle holder 12, for example, by threaded engagement with external threads 14 extending about hub assembly 20. In this manner, this needle cover can be removed from non-patient needle assembly 12 prior to assembly with a needle holder by unthreading the needle cover from external threads 14, and then threading external threads 14 into an internal thread of such a needle holder, as is known in the art.

Operation and use of the blood collection set including the non-patient needle assembly will now be described with reference to FIGS. 1-5. In use, blood collection set 10 is provided including intravenous needle assembly 90 and non-patient needle assembly 12 attached through tubing 84. Alternatively, non-patient needle assembly 12 may be provided as separate from a blood collection assembly including intravenous needle assembly 90 and tubing 84 interconnected. In such a case, non-patient needle assembly 12 is first attached to tubing 84, for example, through connector 86 which is desirably a luer fitting for connection with ferrule 30.

Non-patient needle assembly 12 is provided including a needle cover (not shown) extending over external cannula 50. When preparing the blood collection set for use in a sampling procedure, the needle cover is removed from external cannula 50, and non-patient needle assembly 12 is then attached to a needle holder, such as by threading external threads 14 with internal threads provided on a standard needle holder.

Moreover, a further needle cover (not shown) may extend over intravenous cannula 92 encompassing intravenous puncture tip 94. This needle cover is also removed. Venipuncture is then conducted in known manner, whereby intravenous puncture tip 94 is inserted into a vein of a patient, and an evacuated tube having a pierceable closure is inserted into the needle holder, such that the pierceable closure of the evacuated tube contacts sleeve 80 extending about external cannula 50. When slight pressure is exerted on the evacuated tube, the pierceable closure contacting sleeve 80 causes sleeve 80 to displace, thereby causing non-patient puncture tip 56 to puncture sleeve 80 and, in turn, the pierceable closure of the evacuated tube. At such time, the interior of the evacuated tube and internal lumen 58 of external cannula 50 are in fluid communication. Since the interior of the evacuated tube is at a negative pressure, blood is drawn from the vein of the patient, through intravenous needle assembly 90, through tubing 84 and connector 86, through internal opening 36 of ferrule 30, through internal lumen 48 of internal blunting member 40, through internal lumen 58 of external cannula 50, and into the evacuated tube.

When all desired samples have been drawn, activation of the non-patient needle assembly is accomplished. Activation of the non-patient needle assembly is desirably accomplished while venipuncture is maintained, that is while intravenous puncture tip 94 of intravenous needle assembly 90 is maintained within the vein of the patient. It is noted that intravenous needle assembly 90 may include a blunting member for blunting of the intravenous needle, which blunting operation is separate from blunting of the non-patient needle.

Blunting of the non-patient needle assembly 12 is accomplished by exerting pressure in a direction of arrow 100 on rear face 72 of carriage assembly 60. In particular, during sampling, the top surface of the pierceable closure of the evacuated tube contacts rear face 72 of carriage assembly 60 within the holder. When additional force is exerted against the evacuated tube in a direction of arrow 100, rear face 72 is forced in the direction of arrow 100. Such force causes interference engagement between tapered surface 68 of central nub portion 62 of carriage assembly 60 against face 32 of hub assembly 20. As such, central nub portion 62 of carriage 60 is forced within internal opening 26 of hub assembly 20 due to the configuration of tapered surface 82, thereby causing axial movement of carriage assembly 60 with respect to hub assembly 20.

Since carriage assembly 60 is attached to external cannula 50, axial displacement of carriage assembly 60 with respect to hub assembly 20 causes axial displacement of external cannula 50 with respect to hub assembly 20. Moreover, since internal blunting member 40 is attached to hub assembly 20, axial displacement of external cannula 50 with respect to hub assembly 20 causes second end 54 of external cannula 50 to axially displace with respect to second end 44 of internal blunting member 40. Since blunted tip 44 is positioned short of non-patient puncture tip 56 such that non-patient puncture tip 56 extends beyond blunted tip 44, axial displacement of second end 54 of external cannula 50 with respect to second end 44 of internal blunting member 40 causes relative axial displacement of non-patient puncture tip 56 with respect to blunted tip 46. More particularly, when external cannula 50 is axially displaced in the direction of arrow 100, non-patient puncture tip 56 slides about internal blunting member 40 such that blunted tip 46 is exposed and extends beyond non-patient puncture tip 56, as depicted in FIGS. 4 and 5. As such, non-patient puncture tip 56 is effectively blunted. Non-patient needle assembly 12 can then be appropriately discarded.

As noted, the needle assembly of the present invention may be used in conjunction with a standard needle holder known for use in blood collection. It is also contemplated that the needle assembly of the present invention may be used with a needle holder which includes a mechanism for causing axial displacement of carriage assembly 60 with respect to hub assembly 20 to effect blunting of non-patient puncture tip 56. For example, as opposed to exerting pressure on an evacuated tube extending within the needle holder, a mechanism on or within the needle holder may be activated which causes carriage assembly 60 to axially displace.

The needle assembly of the present invention may be comprised of moldable parts which can be mass produced from a variety of materials including, for example, polyethylene, polyvinyl chloride, polystyrene or the like. Materials will be selected which will provide the proper support for the structure of the invention in its use, but which will also provide a degree of resiliency for the purpose or providing the cooperative relative movement.

While the needle assembly of the present invention has been described in terms of one embodiment for use in connection with a blood collection system, it is further contemplated that the needle assembly could be used with other medical procedures, such as in conjunction with a conventional intravenous infusion set, as which are well known in the art for use with conventional needle assemblies.

What is claimed is:

1. A non-patient safety needle assembly for mounting with a conventional intravenous blood collection set comprising:
    a non-patient hub assembly having opposing first and second ends and a central opening extending through said hub assembly from said first end to said second end, said first end adapted for mounting with a blood collection set,
    an internal blunting member in fixed engagement with said non-patient hub assembly and extending through said central opening of said hub assembly,
    said internal blunting member having a first end concentric with said non-patient hub assembly,
    a second end of said blunting member having a blunted tip and an internal lumen extending through said internal blunting member from said first end of said blunting member to said blunted tip,
    an external non-patient cannula concentric with said internal blunting member and axially displaceable within said non-patient hub assembly, said external non-patient cannula including a non-patient puncture tip adjacent said blunted tip of said internal blunting member,
    said external non-patient cannula adapted for axial displacement with respect to said non-patient hub assembly about said internal blunting member between a first retracted position in which said non-patient puncture tip extends beyond said blunted tip of said internal blunting member and a second activated position in which said blunted tip of said internal blunting member extends beyond said non-patient puncture tip of said external non-patient cannula, and a sleeve extending about said non-patient puncture tip, wherein said non-patient puncture tip can be inserted into and removed from a blood collection tube having a pierceable membrane while said external non-patient cannula is in said first retracted position.

2. A non-patient safety needle assembly as in claim 1, further comprising a carriage assembly integral with said external non-patient cannula and concentric with said internal blunting member, said carriage assembly provided for slidable engagement with said non-patient hub assembly.

3. A non-patient safety needle assembly as in claim 1, further comprising a fitting for engagement with a blood collection set.

4. A non-patient safety needle assembly as in claim 3, wherein said fitting comprises a luer fitting.

5. A non-patient safety needle assembly as in claim 1, further comprising means for attaching said non-patient needle assembly to a holder capable of holding blood collection tubes.

6. A non-patient safety needle assembly as in claim 5, wherein said attaching means comprises threads extending circumferentially about said non-patient hub assembly.

7. A non-patient safety needle assembly as in claim 1, wherein said external non-patient cannula is axially displaceable between said first retracted position and said second activated position in a single axial direction.

8. A non-patient safety needle assembly as in claim 7, further comprising a locking mechanism for preventing axial displacement of said external cannula from said second activated position to said first retracted position.

* * * * *